United States Patent
Brusell et al.

(10) Patent No.: US 8,537,036 B2
(45) Date of Patent: Sep. 17, 2013

(54) TONGUE BASED CONTROL DEVICE FOR TRANSFERRING KEYBOARD COMMANDS

(75) Inventors: Tomas Brusell, Kongsberg (NO); Mats Ekström, Åsa (SE)

(73) Assignee: Brusell Communications AB, Lidingo (SE)

( * ) Notice: Subject to any disclaimer, the term of this patent is extended or adjusted under 35 U.S.C. 154(b) by 526 days.

(21) Appl. No.: 12/747,329

(22) PCT Filed: Sep. 26, 2008

(86) PCT No.: PCT/SE2008/000531
§ 371 (c)(1),
(2), (4) Date: Oct. 4, 2010

(87) PCT Pub. No.: WO2009/078776
PCT Pub. Date: Jun. 25, 2009

(65) Prior Publication Data
US 2011/0032126 A1 Feb. 10, 2011

(30) Foreign Application Priority Data

Dec. 18, 2007 (SE) .................................. 0702813

(51) Int. Cl.
*H03M 11/00* (2006.01)

(52) U.S. Cl.
USPC ............... 341/21; 341/33; 600/590; 702/116

(58) Field of Classification Search
USPC ................... 341/20, 21, 33; 340/4.1, 539.12; 702/116; 600/590
See application file for complete search history.

(56) References Cited

U.S. PATENT DOCUMENTS

| 5,460,186 | A  | * | 10/1995 | Buchhold | ..................... 600/590 |
| 5,989,246 | A  | * | 11/1999 | Kaufmann et al. | ............. 606/15 |
| 7,071,844 | B1 | * | 7/2006  | Moise | ............................. 341/21 |
| 8,044,766 | B2 | * | 10/2011 | Ghovanloo et al. | .......... 340/4.11 |
| 2007/0188472 | A1 | | 8/2007 | Ghassabian | |

FOREIGN PATENT DOCUMENTS

| DE | 19512595 A1 | 10/1996 |
| SE | 9202986 A | 4/1994 |
| WO | 02/075515 A1 | 9/2002 |
| WO | 2006/105797 A2 | 10/2006 |
| WO | 2007/053562 A2 | 5/2007 |

OTHER PUBLICATIONS

International Search Report for PCT/SE2008/000531, mailed Mar. 16, 2009.
McLean, J. G., et al., "Oral Transducer-Controller and Variations for Computer Control," IBM Technical Disclosure Bulletin, vol. 32, No. 12, May 1, 1990, pp. 445-447.
Huo, Xueliang, et al., "A Wireless Tongue-Computer Interface Using Stereo Differential Magnetic Field Measurement," Engineering in Medicine and Biology Society, 2007, 29th International Conference of the IEEE EMBS, Lyon, France, Aug. 23-26, 2007, pp. 5723-5726.

* cited by examiner

*Primary Examiner* — Albert Wong
(74) *Attorney, Agent, or Firm* — Potomac Patent Group, PLLC

(57) ABSTRACT

A device for transferring keyboard commands from a user to an electronic apparatus or machine. An arm intended to be carried by the user as a headset, is provided with signal sensors responding to the presence or pressure of the user's tongue by emitting an electric signal or impulse. A signal unit registers and converts signals from the sensors into corresponding keyboard commands which are then input to the electronic device or machine. The device thus basically works as a keyboard where the signal sensors constitute keys that can be operated solely by the tongue, i.e. without involving the hands.

8 Claims, 1 Drawing Sheet

TONGUE BASED CONTROL DEVICE FOR TRANSFERRING KEYBOARD COMMANDS

TECHNICAL FIELD

The present invention refers to a device for transferring keyboard commands from a user to an electronic apparatus or machine.

BACKGROUND

Keyboards are generally used to input various commands to electronic apparatuses and machines. In this description, the term "keyboard command" is intended to represent all possible types of input that can be made by means of a keyboard, keypad, remote control, control panel or the like for electronic apparatuses and machines, e.g. computers, telephones, TV sets, sound systems, medical equipment, engineering machines, instruments, etc.

Typically, such keyboard commands are input, e.g., for writing or controlling computer programs and applications, by the user pressing keys or buttons with his/her fingers, which however in some situations is not possible or desirable. Hence, there is a need to enable keyboard commands without requiring the use of hands, e.g. for disabled persons or when both hands are busy with other activities such as when driving a car and when operating various machines and instruments. For example, a doctor, dentist or nurse may need to input data to a computer during examination or treatment of a patient requiring work with the hands.

Previously, different solutions have been proposed where the user can control a computer cursor by means of movements of the tongue and/or other parts of the mouth cavity or the face. The previously known solutions of the above typically involve some actuator corresponding to the mouse, which is positioned inside the mouth cavity, e.g. a ball or the like applied at a row of teeth or in the palate, see e.g. DE 195 12 595 A1. However, it may be perceived as a nuisance for the user to have a foreign object in the mouth, particularly in terms of hygienics. It is also necessary to position the actuator properly in the mouth cavity, as well as cleaning and maintaining it, resulting in additional efforts.

WO 02/075515 discloses a solution for controlling a cursor on a computer screen by registering ultrasonic signals that are reflected against the user's tongue and/or mouth cavity, which does not require any device inside the mouth.

There are also solutions for disabled persons based on registration of eye movements. However, this technique is relatively expensive and difficult to realize with sufficient accuracy, further requiring a lot of training of the user. Moreover, the user is not able then to focus his/her eyes on other things.

However, none of the above-mentioned solutions is particularly suitable for relatively easy and swift input of a range of different specific keyboard commands, including e.g. numerals, letters and other characters.

SUMMARY

It is an object of the present invention to overcome or at least reduce the above-mentioned problems, and to obtain a relatively simple and sturdy solution enabling input of keyboard commands to an electronic apparatus or machine, without using the hands.

These objects and others may be accomplished by means of a device for transferring keyboard commands from a user to an electronic apparatus or machine, according to claim 1.

The device comprises at least one arm intended to be carried by the user on the outside of the user's mouth cavity, and having a plurality of signal sensors configured to respond to the presence or pressure of the user's tongue in a limited area or input position in close proximity to each respective sensor by emitting an electric signal or impulse. The device also comprises a signal unit configured to register and convert signals emitted from the sensors into a corresponding keyboard command which is then input to said electronic device or machine.

One or more signal sensors may be of the type capacitive sensor responding to the presence of biological mass in a limited sensing field adjacent to each respective sensor. One or more signal sensors may further be of the type microswitch, inductive sensor or magnetic switch, responding to the presence of the tongue by altering an electric or magnetic field or by contact between two metal plates. By positioning the tongue next to the cheek, or pressing it against the inside of the cheek or around the mouth, a signal sensor of any of the above types can thus be activated to generate a signal.

According to some other possible embodiments, the device may comprise two substantially parallel arms which in use extend above and below the user's mouth, respectively, and/or along the cheek, or an arm branching out to extend above and below the user's mouth, respectively. Each sensor may correspond to at least one specific command. The signal unit may be programmed to create different commands from different combinations of impulses from the sensors. Different activation durations for a specific sensor may further correspond to different commands.

BRIEF DESCRIPTION OF THE DRAWINGS

The present invention is described in more detail below by means of different exemplary embodiments and with reference to the appended drawings.

DETAILED DESCRIPTION OF EMBODIMENTS

Figure 1:
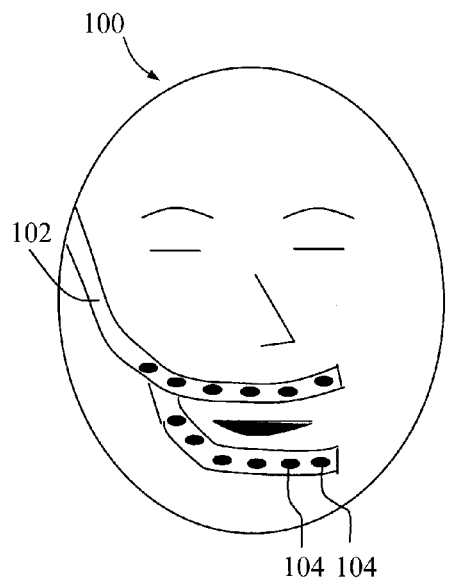
FIG. 1 is a schematic overview of a device for transferring keyboard commands from a user, according to one embodiment.

In FIG. 1, an example of a device is shown for transferring keyboard commands from a user 100, intended to be carried by the user's head as a so-called "headset". The device comprises an arm 102 having a plurality of signal sensors 104 placed along the arm 102 in an area which in use is basically located in close proximity to the outside of the user's mouth cavity. The signal sensors 104 are preferably located in positions that can easily be reached by the user's tongue.

The signal sensors 104 are configured to emit an electric signal or impulse by the presence of the user's tongue or when touched by the skin around the mouth cavity through pressure of the tongue. The device is further configured to register and convert this signal into a corresponding keyboard command which is then input to an electronic device or machine.

For example, the signal sensors 104 may be of the type capacitive sensors configured to respond to the presence of biological mass in a limited sensing field adjacent to each respective sensor, such that when the user places his/her tongue next to one of these sensors, i.e. within its sensing field, an electric signal or impulse will be emitted from the sensor. The capacitive sensors 104 may be calibrated for a suitable sensitivity in order to be easily activated by the tongue whereby a voltage is created at the output of the sensor.

The signal sensors 104 may further be of the type microswitches, inductive sensors or magnetic switches, wherein a switch or sensor located outside the mouth cavity is configured to respond to the presence of the tongue or a pressure thereof inside the mouth cavity, basically in an input position adjacent to each respective switch/sensor by generating a signal or impulse. The signal or impulse can then be generated, e.g., by altering an electric or magnetic field, or by contact between two metal plates or the like, depending on the type of sensor.

For example, the sensors 104 may be calibrated to respond to contact with the cheek, such that the user can press his/her tongue lightly against the inside of the cheek for contacting the sensor in order to activate it and create an input. Sensors of the type capacitive sensors may also be calibrated to respond when the tongue is merely placed at the inside of the cheek in an input position such that the biological mass increases in the sensing field of the sensor and the sensor is activated, even without contacting the skin of the cheek.

Further, a sensor of the type inductive sensor or magnetic switch may e.g. be configured to respond to pressure of the tongue against a metal sheet arranged at the outside of the mouth cavity, wherein the sheet is moved in a direction towards an inductive or magnetic sensor or a contact device, which is then activated and emits a signal. The signal sensors 104 may further be calibrated to respond not until the tongue has been located in an input position such as a sensing field for a certain duration, e.g. one second.

By means of the above-described arrangement, the user is able to input any optional keyboard commands to the electronic device or machine, by moving his/her tongue to different input positions next to the signal sensors, the device thus working as a keyboard where the signal sensors constitute "keys" that can be operated solely by the tongue, i.e. without involving the hands. It is also possible to configure the device to create a multitude of different inputs and functions by activating different combinations of sensors. This device can be realised by means of simple components and is relatively easy for the user to learn how to operate.

Figure 2:
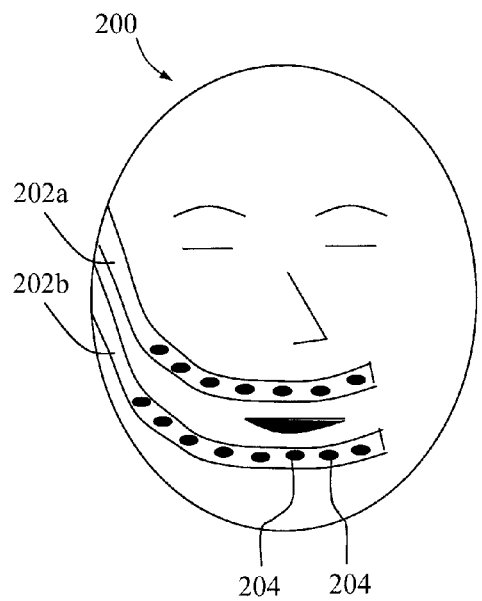
FIG. 2 is a schematic overview of a device for transferring keyboard commands from a user, according to another embodiment.

In FIG. 1, an embodiment is shown where the arm 102 branches off into two arm parts which during use extend above and below the user's mouth, respectively. FIG. 2 illustrates an alternative embodiment of a similar device, carried by a user 200, having two substantially parallel arms 202a, 202b extending along the user's cheek above and below the mouth, respectively. As in FIG. 1, a plurality of signal sensors 204 are arranged on each arm 202a, 202b in suitable positions outside the user's mouth cavity. The arm 102 or arms 202a, 202b may also be designed to extend further on the other side of the mouth in a basically symmetric configuration. As can be understood from the above, the signal sensors 204 may be of the type capacitive sensors, microswitches, inductive sensors or magnetic switches, depending on the practical implementation.

A person skilled in the art will understand that the arm(s) of the device and the positioning of signal sensors thereon can be configured in several different ways within the scope of the invention, depending on the field of use and implementation. For example, the arm having the signal sensors may be branched out into any number of arm parts of any optional direction, length and mutual spacing. Any optional number of signal sensors may further be arranged at any optional positions along the arm(s), in order to create desirable functions. As mentioned above, the device is configured as a headset that can be carried by the user's head, e.g. applied at one ear, or in an arc above the head, or by means of an elastic strap around the head. The invention is not limited to any particular configuration for carrying the device.

Figure 3:
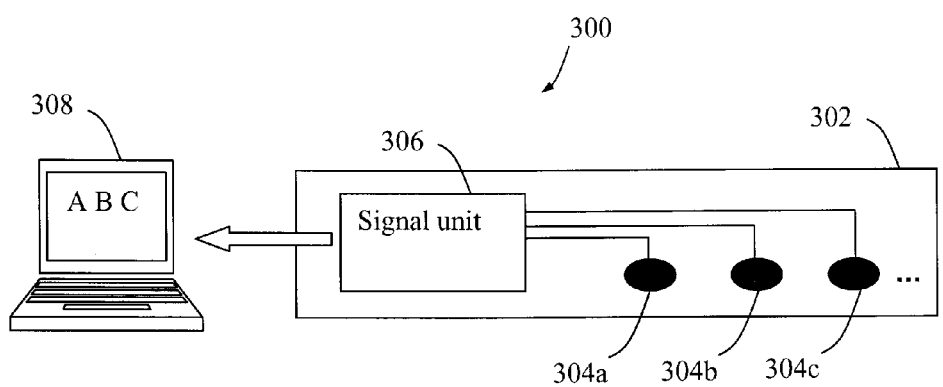
FIG. 3 is a basic drawing illustrating how a device for transferring keyboard commands can be formed in more detail, according to yet another embodiment.

FIG. 3 illustrated in more detail how the invented device can be configured for transferring keyboard commands, according to one possible embodiment. The numeral 300 generally refers to the device for transferring keyboard commands, comprising an arm 302 being shown here schematically with only a few signal sensors 304a,b,c. The device 300 further comprises a signal unit 306 to which the sensors 304a,b,c are connected for registration of signals or impulses therefrom when activated as described above.

The signal unit 306 is configured to convert each signal or impulse from the sensors into a corresponding keyboard command which is then input to an electronic device or machine, in this example a computer 308. For example, each sensor 304a,b,c may correspond to a specific character. In the shown example, the sensor 304a corresponds to the letter A, sensor 304b corresponds to the letter B and sensor 304c corresponds to the letter C. Thus, a user has activated in turn the sensors 304a, 304b and 304c in order to write "ABC" on the computer 308.

The signal unit 306 may also be programmed to create a multitude of commands, e.g. different characters and functions, by registering different combinations of impulses from the sensors. For example, the signal unit 306 may convert a combination of one impulse from sensor 304a immediately followed by one impulse from sensor 304b, into a keyboard command that activates a certain program or function in the computer 308. Furthermore, different activation durations for a certain sensor may correspond to different characters or functions, e.g. 1 second—A, 2 seconds—B, and so forth. The signal unit 306 may also be programmed for different mouse functions on the computer screen in response to impulse registrations from the sensors. Example: sensor 1 directs the cursor downwards, sensor 2 directs the cursor to the left.

Keyboard commands created in this manner may be transferred from the signal unit 306 to the computer 308 through a cable (not shown) or wirelessly. Thus, a transmitter may be connected to the signal unit 306 and transfer the signals wirelessly to a receiver at the computer 308, e.g. by means of IR light or Bluetooth radio. Thus, the invention is not generally limited to any particular transfer mechanism between the signal unit and the electronic device or machine.

Using signal sensors for registering the presence of the tongue as described above may result in the following benefits. Signal sensors of the type capacitive sensor, microswitch, inductive sensor or magnetic switch are generally simple, well-tried, stable and sturdy components of low weight. They can withstand dirt and moisture, be washed, and also withstand relatively high temperatures. Furthermore, their functionality is temperature independent and the activation responsiveness can be calibrated in different ways. The invented device is not limited to any particular field of usage, but may be used, e.g., for controlling computers, telephones, TV sets, sound systems, electric wheelchairs, equipment for disabled persons, medical equipment, industrial process machines, instruments and tools.

Of course, different combinations of the above-described embodiments are possible within the scope of the invention, which is not limited to the disclosed embodiments. For example, different types of sensors may be used jointly in one application, such as capacitive sensors located next to the cheek sides and microswitches or magnetic switches located close to the mouth. The invention is defined by the following claims.

The invention claimed is:

1. A device for transferring keyboard commands from a user to an electronic apparatus or machine, the device comprising:
    at least one arm carried by the user on the outside of the user's mouth cavity, said arm having a plurality of signal sensors configured to respond to the presence or pressure of the user's tongue or mouth in a limited area or input position in close proximity to each respective signal sensor by emitting an electric signal or impulse wherein at least one of the signal sensors is of the type capacitive sensor configured to respond to the presence of biological mass in a limited sensing field, and
    a signal unit configured to register and convert signals emitted from the signal sensors into a corresponding keyboard command which is then input to said electronic apparatus or machine.

2. A device according to claim 1, wherein at least one of the signal sensors is of the type microswitch, inductive sensor or magnetic switch, configured to respond to the presence or pressure of the tongue by altering an electric or magnetic field or by contact between two metal plates, such that said signal or impulse is generated.

3. A device according to claim 1, wherein the device comprises two substantially parallel arms configured to extend above and below the user's mouth, respectively, and/or along the cheek, or an arm branching out to extend above and below the user's mouth, respectively.

4. A device according to claim 1, wherein each sensor corresponds to at least one specific command.

5. A device according to claim 1, wherein the signal unit is programmed to create different commands from different combinations of impulses from the sensors.

6. A device according to claim 1, wherein different activation durations for a specific sensor correspond to different commands.

7. A device according to claim 1, wherein the signal sensors are calibrated to respond not until the tongue has been located in a respective input position for a certain duration.

8. A device according to claim 1, configured to control any of the following types of electronic apparatuses or machines: computers, telephones, TV sets, sound systems, electric wheelchairs, equipment for disabled persons, medical equipment, industrial process machines, instruments and tools.

* * * * *